(12) United States Patent
Uhlhorn

(10) Patent No.: US 7,744,216 B1
(45) Date of Patent: Jun. 29, 2010

(54) DISPLAY SYSTEM INTENSITY ADJUSTMENT BASED ON PUPIL DILATION

(75) Inventor: Brian L. Uhlhorn, St. Paul, MN (US)

(73) Assignee: Lockheed Martin Corporation, Bethesda, MD (US)

( * ) Notice: Subject to any disclaimer, the term of this patent is extended or adjusted under 35 U.S.C. 154(b) by 924 days.

(21) Appl. No.: 11/327,136

(22) Filed: Jan. 6, 2006

(51) Int. Cl.
*A61B 3/10* (2006.01)
*A61B 3/14* (2006.01)

(52) U.S. Cl. .................. 351/204; 351/206; 351/208; 351/209

(58) Field of Classification Search ......... 351/205–246; 348/51–55; 382/131
See application file for complete search history.

(56) References Cited

U.S. PATENT DOCUMENTS

| | | | |
|---|---|---|---|
| 3,533,683 A | 10/1970 | Stark et al. | 351/206 |
| 3,598,107 A | 8/1971 | Ishikawa et al. | 600/473 |
| 5,976,017 A * | 11/1999 | Omori et al. | 463/32 |
| 6,090,051 A * | 7/2000 | Marshall | 600/558 |
| 6,456,438 B1 * | 9/2002 | Lee et al. | 359/630 |
| 6,547,720 B1 * | 4/2003 | Street | 600/111 |
| 6,752,498 B2 * | 6/2004 | Covannon et al. | 351/240 |
| 7,480,396 B2 * | 1/2009 | Teiwes et al. | 382/117 |
| 2002/0186348 A1 | 12/2002 | Covannon et al. | 351/240 |
| 2004/0145539 A1 | 7/2004 | Okamoto et al. | 345/8 |
| 2005/0007256 A1 | 1/2005 | DeLine et al. | 340/815.4 |
| 2005/0024586 A1 | 2/2005 | Teiwes et al. | 382/128 |
| 2005/0062684 A1 | 3/2005 | Geng | 345/32 |
| 2005/0094098 A1 | 5/2005 | Morita et al. | 351/203 |
| 2005/0131607 A1 | 6/2005 | Breed | 701/45 |
| 2005/0152590 A1 * | 7/2005 | Thieret et al. | 382/131 |
| 2008/0188777 A1 * | 8/2008 | Bedziouk et al. | 600/595 |

FOREIGN PATENT DOCUMENTS

| | | |
|---|---|---|
| EP | 0 215 818 B1 | 7/1991 |
| WO | 02/064031 A2 | 8/2002 |
| WO | 02/064031 A3 | 8/2002 |

OTHER PUBLICATIONS

Lewis, "In the Eye of the Beholder, Scanning light beams to the retina could revolutionize displays for everything from cellphones to games," IEEE Spectrum, May 2004, pp. 24-28.
Rose, M., "Microdisplays: Coming Soon to an Eye Near You?" *Photonics Spectra*, Sep. 2008: 68-69.

* cited by examiner

*Primary Examiner*—Mohammed Hasan
(74) *Attorney, Agent, or Firm*—Mueting, Raasch & Gebhardt, P.A.

(57) ABSTRACT

A method and/or system of adjusting light output intensity of a display system includes providing a display system that provides information to a user. Dilation of a pupil of the user is monitored (e.g., using an imaging device) and adjustment of the light output intensity of the display system is performed as a function of the monitored dilation of the pupil of the user. Yet further, for example, such adjustment of light output intensity may also be performed as a function of the monitored ambient light intensity in addition to the monitored dilation of the pupil of the user.

20 Claims, 5 Drawing Sheets

DISPLAY SYSTEM INTENSITY ADJUSTMENT BASED ON PUPIL DILATION

BACKGROUND OF THE INVENTION

The present invention relates generally to display systems and methods relating thereto. More particularly, the present invention pertains to adjustment of to display system intensity.

Various types of display systems are available which provide information to a user. For example, computer screens, direct ocular projection systems, heads up displays, vehicle dashboard displays, instrument panels, night-sight scopes, range finders, sighting scopes, etc. In many circumstances, as information (e.g., images) are viewed by individuals using the display system (e.g., on a screen or projected directly into the eye), the intensity or brightness of the information (e.g., images) should be adjusted to an individual's needs. For example, such needs may include looking for more detail in a washed-out image or protecting an individual's eyes from damage caused by too much light.

Further, for example, in a direct ocular projection display system, light beams are scanned to the retina of a user. It is therefore important to prevent damage to the eyes from an over intense scanned beam.

Still further, for example, an individual may be using a night-sight scope or other display in an otherwise dark environment. If the intensity of the display or light output to the individual's eyes of the night-sight scope is too high, then when the individual is no longer using the night-sight scope and attempts to visualize their darker surroundings, the individual is presented with difficulty adjusting from the bright light output of the night-sight scope to the darker surroundings. In other words, the individual may become "night blind" in critical situations, such as when in combat. Such night blindness may also occur in situations such as when an individual is driving an automobile or other vehicle.

In many circumstances, the intensity or brightness of such display systems is controlled by a static setting or predefined settings. Such static setting or predefined settings do not necessarily provide the intensity or brightness necessary for adapting to an individual's particular needs.

In addition, generally, in order to change the intensity or brightness of a display system, an individual is required to physically respond and change a setting to adjust intensity. For example, an individual may be required to flip a switch, turn a dial, move one or more actuators, etc. Such need to physically respond when adjusting intensity or brightness of a display system may waste valuable time in time critical situations. For example, such time critical situations may occur when an individual's eyes are in danger of being damaged by a high light output, or when in a combat situation.

SUMMARY OF THE INVENTION

The present invention monitors the dilation of an individual's pupil or pupils and uses such information concerning the dilation of the individual's pupil or pupils to adjust intensity of light output of a display system which the individual is using. In one or more embodiments, the detection of ambient lighting conditions may also be employed in adjusting the intensity of the light output.

A method of adjusting light output intensity of a display system, according to the present invention, includes providing a display system to provide information to a user and monitoring dilation of a pupil of the user. Light output intensity of the display system is then adjusted as a function of the monitored dilation of the pupil of the user.

In one embodiment, the display system is used to provide information to a user at a user location, and the method further includes monitoring ambient light intensity at the user location. In such a case, light output intensity of the display system is adjusted as a function of the monitored ambient light intensity and the monitored dilation of the pupil of the user.

In another embodiment of the method, the monitoring of the dilation of the pupil results in a measurement of pupil size. An expected dilation of the pupil of the user may be calculated as a function of the monitored ambient light intensity, and the measurement of pupil size may be compared to the expected dilation of the pupil of the user.

In another embodiment of the method, monitoring the dilation of the pupil results in a measurement of pupil size. The measurement of pupil size may be compared to a minimum pupil size, and the light output intensity of the display system may be automatically reduced (e.g., automatically ceasing light output) if the measurement is less than the minimum pupil size.

Yet further, in another embodiment, the display system may include a direct ocular projection system operable for projecting an image to the user, or may include at least one of a screen being viewed by the user, a projector, a laser, a heads up display, a vehicle dashboard display, a night-sight scope, a range finder, and/or a sighting scope.

A display system to provide information to a user according to the present invention includes a light output device to generate light output and an imaging device operable to capture one or more images of an eye of a user that is using the display system. The display system further includes a processing apparatus operable to receive image data from the imaging device representative of one or more images of the eye of the user. The processing apparatus is further operable to determine at least one pupil size measurement using the image data representative of the one or more images of the eye of the user and to generate a control signal as a function of the at least one pupil size measurement for use in adjusting light output intensity of the light output device.

In one embodiment of the system, the system further includes a light sensor operable to detect ambient light intensity and the processing apparatus is operable to receive an ambient light intensity signal from the light sensor. Further, the processing apparatus is operable to generate a control signal as a function of a detected ambient light intensity and the at least one pupil size measurement for use in adjusting light output intensity of the light output device.

In another embodiment of the system, the processing apparatus is further operable to calculate expected dilation of the pupil of the user based on the detected ambient light intensity and compare the at least one pupil size measurement to the expected dilation of the pupil of the user for use in generating the control signal.

In yet another embodiment of the system, the processing apparatus is further operable to compare the at least one pupil size measurement to a pupil minimum size and automatically reduce (e.g., cease) the light output intensity of the light output device based on the comparison (e.g., if the measurement is less than the minimum pupil size).

In one or more embodiments of the display system, the display system includes a direct ocular projection system operable for projecting an image to the user, and/or a display system, that includes at least one of a screen being viewed by the user, a projector, a laser, a heads up display, a vehicle dashboard display, a night-sight scope, a range finder, and/or a sighting scope.

Another display system, according to the present invention, includes a light output device operable to generate a loud output and an imaging apparatus for capturing one or more images of an eye of a user using the display system at a location. A light sensor apparatus is used to detect ambient light intensity at the location. A processing apparatus is operable to receive an ambient light intensity signal from the light sensor apparatus and image data from the imaging apparatus representative of one or more images of the eye of the user. Further, the processing apparatus determines at least one pupil size measurement using the image data representative of the one or more images of the eye of the user and generates a control signal as a function of the detected ambient light intensity and the at least one pupil size measurement for use in adjusting light output intensity of the light output device.

The above summary of the present invention is not intended to describe each embodiment or every implementation of the present invention. Advantages, together with a more complete understanding of the invention, will become apparent and appreciated by referring to the following detailed description and claims taken in conjunction with the accompanying drawings.

DETAILED DESCRIPTION OF THE EMBODIMENTS

Figure 1:
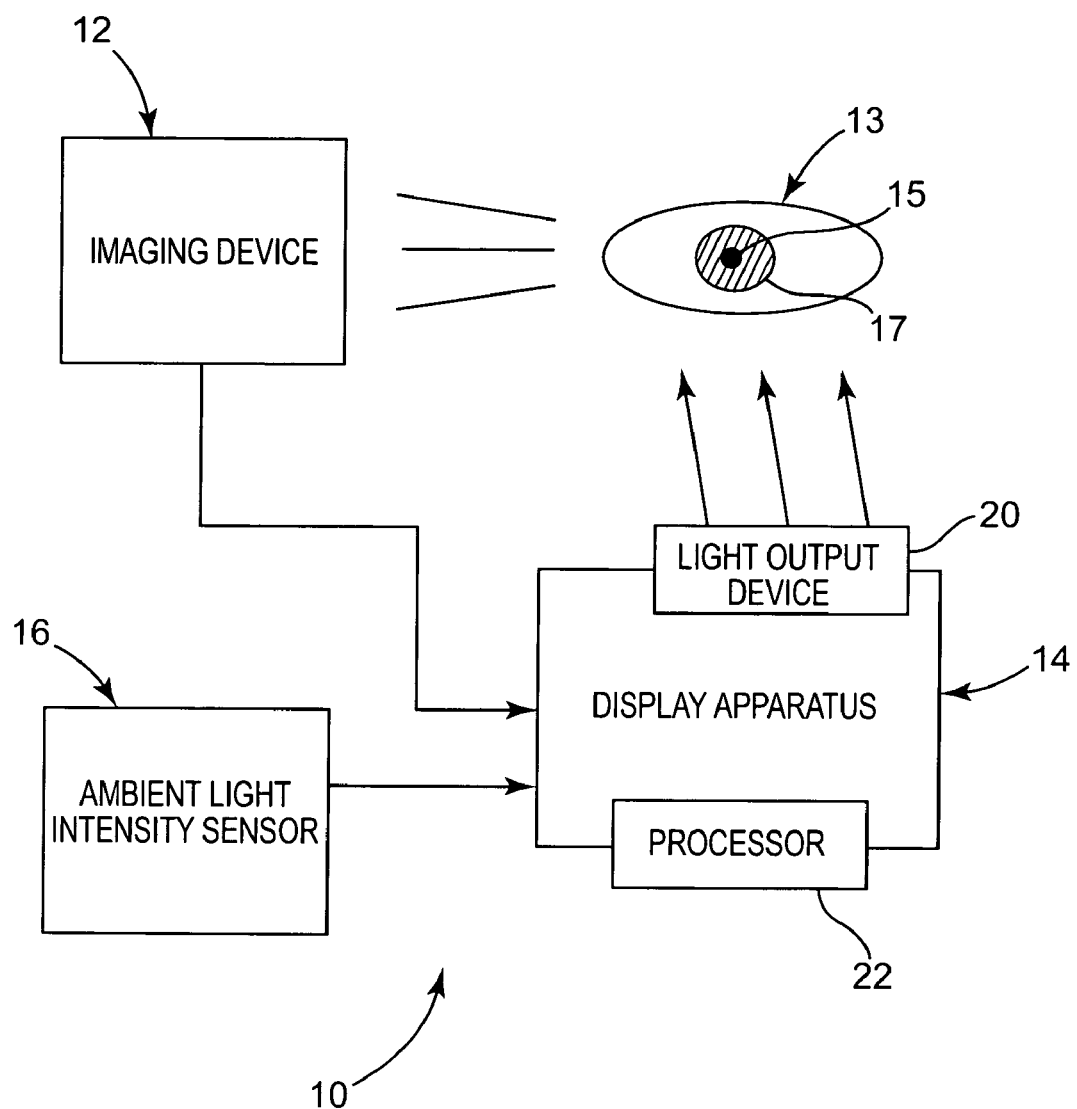
FIG. 1 shows an exemplary display system according to the present invention for adjusting intensity of the display system as a function of the monitoring of the dilation of a pupil of a user.

Generally, an exemplary display system 10, according to the present invention, shall be illustratively described with reference to FIG. 1. One or more embodiments of the display system 10 and components thereof, along with methods associated with the operation of the display system 10, shall further be described in more detail with reference to FIGS. 1-5.

As further described in detail herein, display system 10 includes a display apparatus 14 for use in providing information to a user capable of perceiving such information with use of one or more eyes 13 thereof. The display apparatus 14 includes a light output device 20 for use in providing such information to a user. Further, the display apparatus 14 may further be associated with a processing apparatus 22 of the display system 10 to generate a control signal for use in adjusting light output intensity of the light output device 20.

The display system 10 also includes an imaging device 12 operable to capture one or more images of an eye 13 of a user that is using the display system 10. In one or more embodiments, the processing apparatus 22 is operable to receive image data from the imaging device 12 representative of one or more images of the eye 13 of the user (or portions thereof) and, for example, determines at least one pupil size measurement using the image data representative of the one or more images of the eye 13 of the user for use in generating a control signal for adjusting light output intensity of the light output device 20.

Still further, the display system 10 may include a light sensor 16 to detect ambient light intensity, for example, at the location at which display system 10 is being used. In one or more embodiments, processing apparatus 22 is operable to receive at least an ambient light intensity signal from the light sensor 16. Yet further, in one or more embodiments, the processing apparatus 22 may be operable to generate a control signal as a function of the detected ambient light intensity as detected by ambient light intensity sensor 16 and as a function of pupil size determined from image data provided by imaging device 12.

The display apparatus 14 incorporated in display system 10 may be a portion of one or more various display systems suitable for providing one or more various types of information to a user. For example, such information may be graphical information, textual information, video information, images, holographic information, image enhancement, image annotation, visual cues, or the like.

For example, the display apparatus 14 of the display system 10 may include or may form a part of any type of display screen being viewed by a user (e.g., a display screen controlled by one or more processing apparatus), a computer screen, a flat screen, a liquid crystal display (LCD), a heads up display, display goggle (e.g., LCD goggles), a laser or light emitting diode (LED) display, cell phones, personal digital assistants (PDAs), backlit display screens, see-through displays, non-see-through displays, a vehicle dashboard display, an instrument panel, a night-sight scope, a range finder, a sighting scope, a direct ocular projection system, heads up display, projection display, laser projection display, laser system, or any other type of display system that provides information to a user where the benefits of controlling a light output device thereof as a function of the monitored dilation of at least one pupil of a user is beneficial.

As will be apparent, depending upon the type of display apparatus 14 employed by the present invention, light output device 20 may take one or more various different forms. For example, the light output device 20 may be that of a screen (e.g., LED, LCD, etc.), a projector, a laser, the backlight of a display, elements reflecting a light source, screen (CRT), LED elements, incandescent elements, or any other light emitting device.

In one particular embodiment, the display system 10 includes a direct ocular projection system. For example, a direct ocular projection system is operable for projecting an imaging onto the retina of the user. One or more embodiments of such a system are described in the article by John R. Lewis entitled, "In the eye of the beholder," IEEE Spectrum, May 2004, pages 24-28.

As the present invention may be beneficial for use with one or more various types of display systems, details with respect to the optics, the light output devices, the processing apparatus, the structure and/or configuration of such displays, shall not be described herein. The present invention provides for one or more various embodiments of systems and/or methods for adjusting light output intensity of display systems without a particular focus on the type of display system. However, one or more display systems may benefit to a greater degree from adjustment of light output intensity based on the monitored dilation of a pupil of a user of the display system. For example, some display systems may be more harmful than others if light output intensity of the display system exceeds a certain level.

Imaging device 12 may include any suitable imaging device for capturing one or more images of the eye 13 of a user that is using the display system 10. At least in one embodiment, the imaging device 12 must provide an image of at least one of the pupils 15 of the eye 13 of the user such that the pupil size can be determined. Although monitoring of the size of both pupils of the user may be beneficial (e.g., such pupil size may be average for accuracy of measurements), monitoring of one or both of the pupils may be employed according to the present invention.

The imaging device 12 provides one or more frames of images with a suitable field of view, and depending upon the display system 10 being employed by the user, the imaging device 12 may be a part of the display apparatus 14 and structurally incorporated therewith and/or mounted apart from the display apparatus 14. For example, with respect to a vehicle dashboard display, imaging device 12 may be mounted as part of the dashboard display with a field of vision that images the face of a user, or the imaging device 12 may be mounted apart from the dashboard display as part of the mirror or visor.

One or more various apparatus may be used to maintain a field of view that includes the eye 13 of the user. For example, the imaging device 12 may be moved manually or automatically in one or more direction (e.g., based on a one or more tracking algorithms), rotated, focused, auto-focused, voice-responsive, motion sensitive, LADAR (LAser Detection And Ranging) tracked, or LADAR (Light Detection And Ranging) tracked.

The imaging device 12 may be any suitable apparatus for providing image data to be used for monitoring the size of the pupil of the user. For example, the imaging device 12 may be a suitable camera, a CCD apparatus, a LADAR or LIDAR imaging apparatus, a microwave or radar imaging device, etc.

The ambient light intensity sensor 16 may be part of imaging device 12 or may be a separate sensor suitable for sensing ambient light at the location that display system 10 is being used. For example, the ambient light intensity sensor 16 may include a photo cell, a photo transistor, or a CMOS sensor. Associated circuitry provides for a detection signal to be provided to processing apparatus 22 for use by display system 10, as further described herein.

The processing apparatus 22 of display system 10 may include any processing components operable to execute code to provide for the generation of a control signal as a function of at least the monitored dilation of a pupil of a user of the display system 10. The system may be implemented using software executable on the processing apparatus 22 or any other specialized hardware that may also provide the same functionality required to provide a user with suitable light output intensity according to the present invention.

The processing apparatus 22 may include one or more processors operating in one or more various architectural configurations (e.g., in parallel). One will recognize that the type of display system 10 employed by the present invention will determine the necessary processing requirements. For example, a direct ocular projection system may require more processing capabilities than an instrument panel of a dashboard. In other words, any suitable processing apparatus 22, along with one or more various peripheral devices to be used in combination therewith, capable to of carrying out the functionality as described herein may be employed according to the present invention.

Further, for example, the present invention may be implemented using one or more program routines executing on programmable processing apparatus having adequate data storage capacity, input devices, and output devices. Program code and/or logic described herein is applied to input data to perform functionality described herein and generate desired output information. The output information may be applied as an input to one or more other devices and/or processes in known fashion (e.g., control of light output device). Any program or code used to implement the present invention may be provided in any programming language (e.g., high level procedural and/or object-orientated) to communicate with the processing apparatus and obtain the desired functionality.

One will recognize that processor apparatus 22 may control the imaging device 12 (e.g., camera) such that images may be constantly received and processed by the processing apparatus 22 to determine pupil dilation and control illumination of display system 10, accordingly.

As further described herein with reference to FIGS. 1-5, various embodiments may utilize the monitoring of the dilation of an individual's pupil for the control of light output intensity of a display system. Although various other embodiments are described herein, in one embodiment, a camera is monitoring the dilation of an individual's pupil as well as the ambient lighting conditions. The camera may be part of a direct ocular projection system or serving some other purpose. The feedback from the individual's pupil dilation (e.g., processed image data that results in a pupil size measurement) is then used to adjust the intensity of the light output from a screen, projector, laser, etc. The measurement of ambient light may provide a way to calculate expected dilation diameter. If the diameter of pupil reaches a defined minimum value, this could trigger an automatic shut-off, preventing potential damage to the eye of the user.

As mentioned in the Background of the Invention section herein, generally, intensity or brightness adjustment has been conventionally performed manually or through feedback from only ambient conditions. According to the present invention, at least in one embodiment, the intensity or brightness adjustment may be done automatically based on an individual's response rather than by a static setting or predefined settings. At least in one embodiment, this may allow for optimum settings for a particular individual. Also, as a safety shut-off, one embodiment of the present invention may react to the individual's biological response, saving time over a system that requires an individual to physically respond, like flipping a switch.

Figure 2:
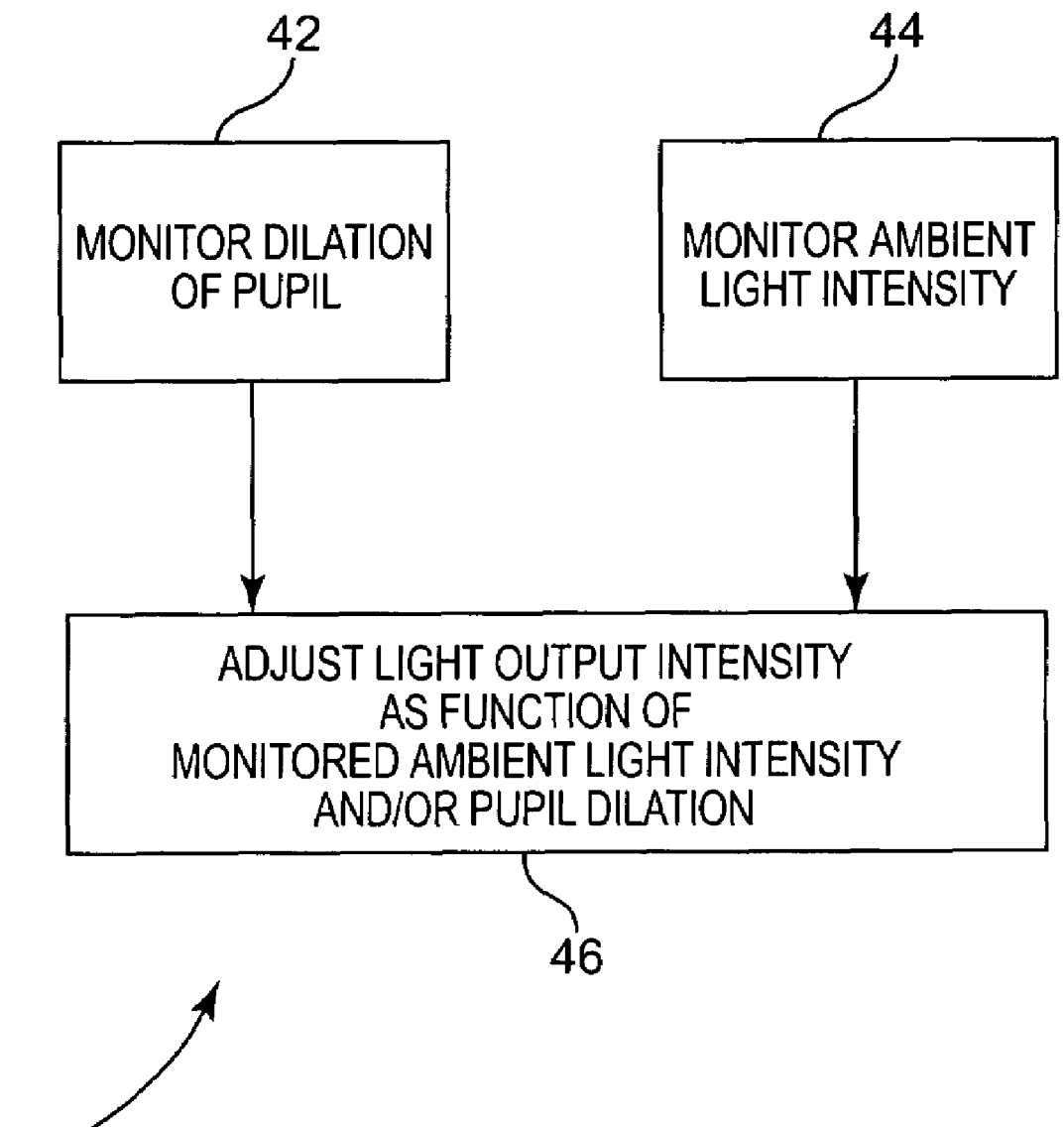
FIG. 2 is a general flow diagram of one exemplary light output intensity adjustment method according to the present invention.

Generally, as shown in FIG. 2, an exemplary light output intensity adjustment method 40 is illustrated which may be implemented using the display system 10 shown in FIG. 1. The light output intensity adjustment method 40 includes monitoring dilation of the pupil of a user of the display system 10 (block 42). Further, the method 40 may also include monitoring ambient light intensity (block 44). The light output intensity of the light output device 20 of the display system 10 is then adjusted as a function of the monitored ambient light intensity and/or the monitored pupil dilation (block 46).

Monitoring the dilation of the pupil 15 of the eye 13 of a user of the display system 10 may be implemented in one or more various manners. For example, FIG. 1 shows a simplified drawing of the eye 13 showing iris 17 and pupil 15. As shown, the pupil 15 is a black, light receptive orifice, while the iris 17 may have any of a broad range of hues and may be irregularly pigmented. The iris 17 and the pupil 15 are closely related in function. A function of the iris 17 is to control the size of the pupil 15. Therefore, in addition to the visible features of iris 17 relating to pigmentation, a number of visible features relate to the movements made by iris 17 in order to contract and dilate pupil 15.

In general, iris 17 may be divided into the ciliary area, which is an annular region at its periphery, and the pupil area, which is an annular region bordering pupil 15. Further, in general, the tissue of the iris 17 is soft and loosely woven, and the illumination which enters the pupil 15 and falls on the retina of the eye 13 controls muscles in iris 17, causing the size of pupil 15 to grow larger or smaller to to regulate the amount of light entering pupil 15. The change in the size of pupil 15 results from involuntary reflexes and is not under conscious control.

As shown in FIG. 1, the pupil 15 may not be exactly circular in shape and its deviation from a circle is a visible characteristic. As the visible features of iris 17 and pupil 15 vary depending on illumination, the monitoring of the eye 13 may be performed for use in adjusting light output from a display system.

As described herein, imaging device 12 provides one or more images of the eye (e.g., a plurality of frames) for analysis by processing apparatus 22. Processing apparatus 22 may perform various functions on the image data representative of the eye 13 in order to determine a pupil size measurement. As used herein, pupil size measurement refers to one or more measurements related to the pupil and, consequently, the corresponding pupil area of the iris bordering the pupil 15. For example, such measurements may include, but are clearly not limited to, an area occupied by the pupil in the image, a diameter measured for the pupil, a radii measured for the pupil, a perimeter measurement of the pupil or the border of the pupil area, rate of change of any of the pupil measurements, or any other measurement parameter associated with the pupil suitable for providing information concerning the size of the pupil 15.

Such processing or analysis of the image data may include use of a boundary detection algorithm or an edge detection algorithm which may, for example, detect an abrupt gray level change between the pupil 15 and the iris 17. One or more algorithms for performing pupil size measurement is disclosed in, for example, U.S. Pat. No. 3,598,107 issued Aug. 10, 1971 to Ishikawa et al., entitled "Pupillary Motion Observing Apparatus, and U.S. Pat. No. 3,533,683 issued Oct. 13, 1970 to Stark et al., entitled "Dynamic Pupillometers Using Television Camera System." Further, for example, a Hough transform algorithm for detecting circles, which maps curves into the transform spaces according to characteristics such as curvature, could be used on a boundary or edge which is detected. Yet further, alternatively, the received image or images could be subjected to a thresholding algorithm after which a region growing or aggregation algorithm, such as a blob analysis algorithm, could be performed by locating the largest connected region of pixels with intensity values below threshold.

Yet further, since the pupil is central, the region could be grown outward from a central dark pixel in the image, progressively aggregating the adjacent dark pixels until the pupil boundary is reached, beyond which adjacent pixels will not be dark. This could provide a measurable pupil size and a location, as the center of the pupil may be determined from its boundary.

It will be recognized that any number of algorithms may be used to obtain a pupil size measurement according to the present invention. The present invention is not limited to any particular algorithm listed herein. However, some algorithms may provide advantages not provided by others.

Figure 3:
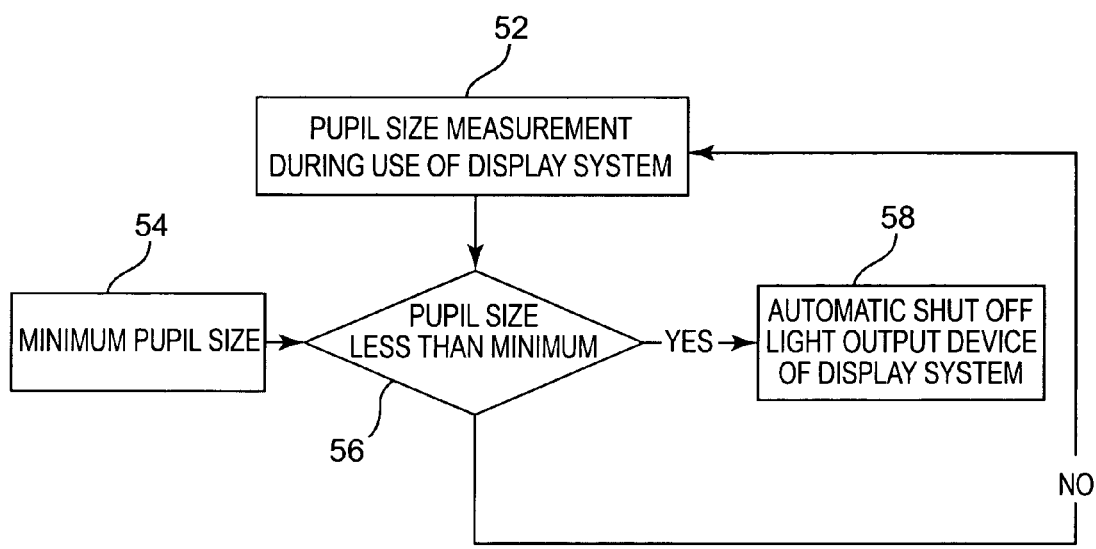
FIG. 3 is a flow diagram of one exemplary automatic shut-off method according to the present invention.

In one embodiment, as shown in FIG. 3, the light output intensity adjustment method 40 takes the form of an automatic shut-off method 50. The pupil size measurement is determined during use of display system 10 (block 52). For example, the area occupied by the pupil 15 of the user of display system 10 is measured (e.g., image data of the eyes of the user are analyzed and a pupil size measurement is generated by processing apparatus 22).

Further, a minimum pupil size is also provided (block 54). The minimum pupil size may be determined in one or more various manners. For example, minimum pupil size may be generated by statistical analysis of pupil size over a larger population. Further, minimum pupil size may be determined on an individual basis by testing an individual's pupil reaction over a range of illumination or light intensity of the user's eye 13. Still further, minimum pupil size may be determined by previously stored calibration measurements, or exceeding a difference from initial pupil size.

The actual pupil size measurement generated during use of a display system 10 (block 52) is then compared to the minimum pupil size (block 54) to determine whether the pupil size is less than the minimum pupil size (block 56) so as to, for example, prevent potential damage to the eye 13 of a user. If pupil size is less than the minimum, an automatic shut-off command is provided to light output device 20 and light output device 20 is immediately automatically reduced (block 58). Such automatic reduction of the light intensity from the light output device 20 may further include entirely shutting off the light output device 20. If pupil size is not less than the minimum pupil size, then the display system 10 continues to monitor the pupil 15 of the user and generate pupil size measurements during its use (block 52).

Figure 4:
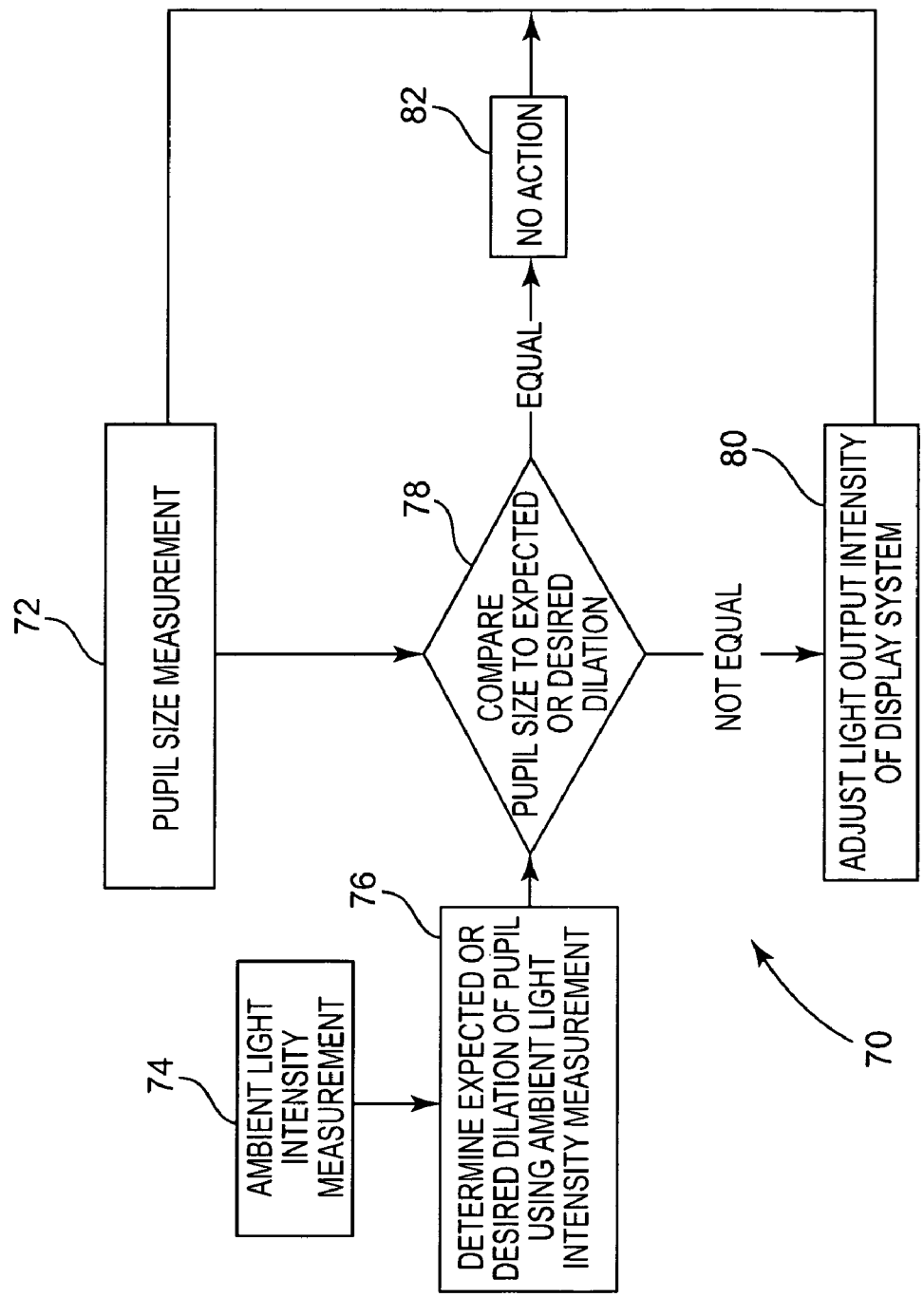
FIG. 4 is yet another flow diagram of an exemplary light output intensity adjustment method according to the present invention.

Another embodiment of a light output intensity adjustment method 70 is shown in FIG. 4. As shown therein, pupil size measurements are continually provided as part of monitoring the eye 13 of the user having access to display system 10. In other words, for example, processing apparatus 22 receives image data from imaging device 12 (e.g., camera) and generates one or more pupil size measurements therefrom (block 72).

Further, ambient light intensity measurements are also provided (block 74). Such ambient light intensity measurements may be made by ambient light intensity sensor 16 or as a part of the imaging data from imaging device 12.

An expected or desired dilation of the pupil 15 of the user may be determined by processing apparatus 22 using the ambient light intensity measurement (block 76). For example, depending upon ambient light conditions, it may be desirable for pupil size to be at a predetermined dilation, but no greater. For example, in the use of a night-sight scope, a user will want to be able to adjust quickly to darker ambient conditions when not using the night-sight scope. As such, depending upon the ambient conditions at the location where the display system 10 is being used, an expected or desired dilation of the pupil size can be generated. In other words, the conditions of the location of the display system may be used to control light output intensity of the display system such that an expected or desired dilation of the pupil 15 of the user is achieved.

As shown in FIG. 4, the pupil size measurement (block 72) is compared to the expected or desired dilation of the pupil as determined using ambient light intensity measurement (block 78). If the pupil size measurement is not equal to the expected or desired dilation, a command is generated by processing apparatus 22 for use in adjusting light output intensity of the display system 10 (block 80). However, if pupil size measurements are equal to the expected and/or desired dilation of the pupil, then no action (block 82) is taken and continual monitoring of pupil size is carried out, as shown by the further generation of pupil size measurements (block 72).

In continuing discussion with respect to the night-sight scope illustration, with the light output intensity adjusted for the display system (block 80), a desired dilation of the pupil is achieved as the user is using the night-sight scope. However, when the user is not using the night-sight scope and is exposed to the ambient conditions, night blindness is prevented.

Figure 5:
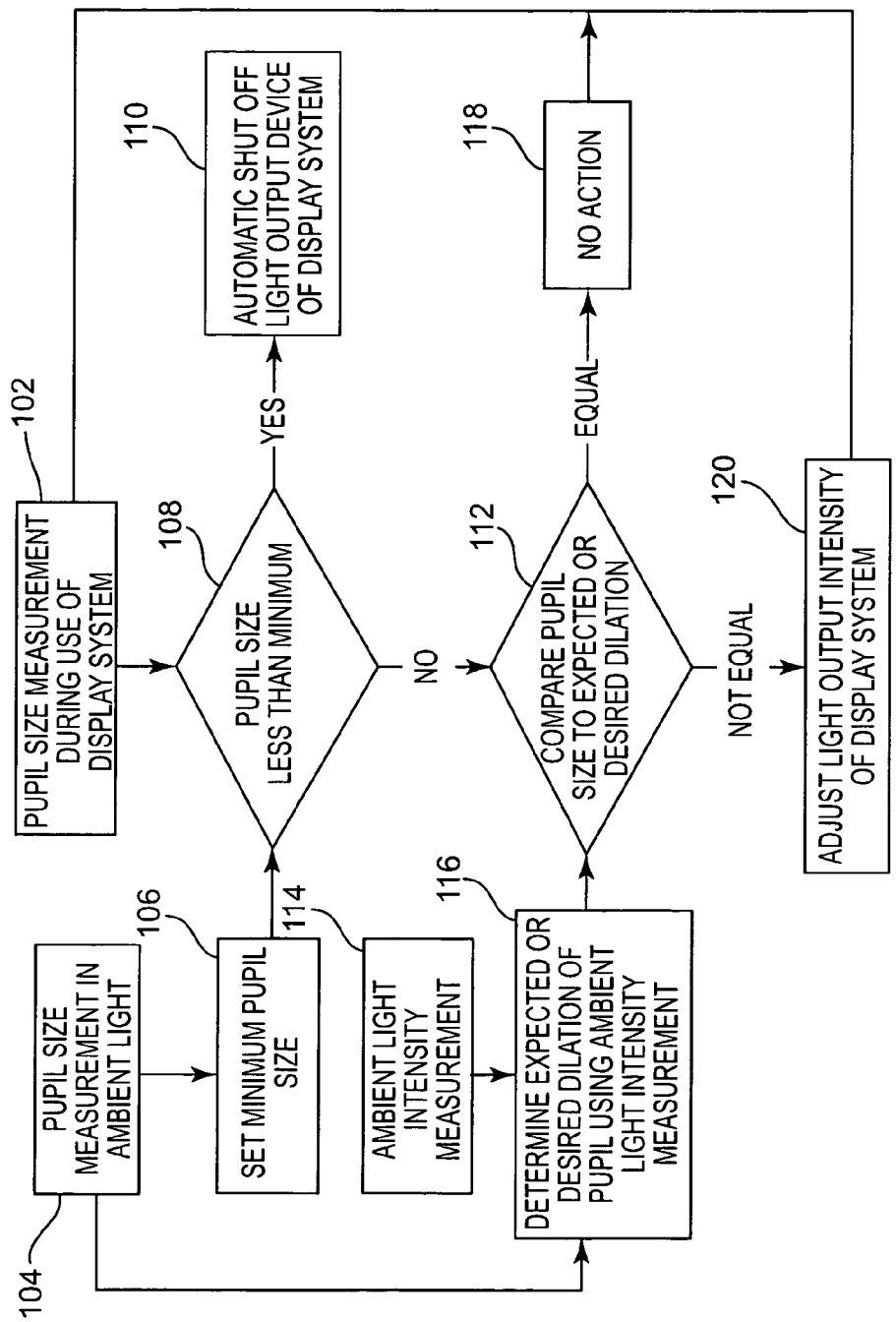
FIG. 5 is still further another flow diagram of yet another exemplary light output intensity adjustment method according to the present invention.

FIG. 5 is yet another illustrative embodiment of a light output intensity adjustment method 100, according to the present invention, incorporating one or more various techniques for using the monitoring of the user's pupil 15 to adjust the light output intensity of a display system 10. As shown in FIG. 5, pupil size measurements are obtained in ambient light (block 104). For example, processing apparatus 22 receives image data from imaging device 12 when the user is not employing the display system 10.

Such a pupil size measurement in ambient light may be used to set a minimum pupil size (block 106). For example, minimum pupil size may be set within a certain range of the pupil size measurement taken in ambient light (block 104) to prevent harm to the user's eyes.

Yet further, ambient light intensity measurements (block 114) may be provided along with the pupil size measurements taken in ambient light (block 104). Such pupil size measurements taken in ambient light (block 104) and ambient light intensity measurements (block 114) may be used to determine expected or desired dilation of the pupil of the user using the ambient light intensity measurements (block 116). Such a determination may be similar to that as described with reference to block 76 of FIG. 4. For example, to prevent night blindness, desired pupil size may be set within a certain range of the pupil size measurement taken in ambient light (block 104) (e.g., no less than 20% of the pupil size measurement taken in ambient light).

During use of the display system, image data from imaging device 12 is used by processing apparatus 22 to generate pupil size measurements (block 102), as otherwise described herein. Such pupil size measurements during use of the display system 10 are compared to the set minimum pupil size (block 108) to determine whether to automatically reduce and/or even automatically shut-off light output device 20 of display system 10 (block 110). If an automatic shut-off or substantial reduction in light output device 20 is not necessary, then the pupil size measurements (block 102) are compared to the expected or desired dilation (block 112) so as to determine whether the light output intensity of the light output device 20 of display system 10 requires adjustment.

In other words, if the feedback of pupil size measurements when compared to the expected or desired dilation are not equal, then an appropriate adjustment (e.g., an increase or decrease in light output intensity) is carried out (block 120). For example, processing apparatus 22 generates a signal for controlling light output device 20 and the intensity thereof. If the pupil size measurements (block 102) are compared to the expected or desired dilation and match such expected or desired dilation, then no action is required (block 118) and pupil monitoring continues as the display system 10 is used.

One skilled in the art will recognize that various manners of using the pupil monitoring data are contemplated according to the present invention and only a few exemplary embodiments are described herein. As such, the present invention is not to be taken as limited to only those embodiments specifically set forth herein.

All patents and references cited herein are incorporated in their entirety as if each were incorporated separately. This invention has been described with reference to illustrative embodiments and is not meant to be construed in a limiting sense. As described previously, one skilled in the art will recognize that various other illustrative exemplary display systems may be provided which utilize various combinations of the elements described herein and/or are suitable for carrying out the functionality described herein. Various modifications of the illustrative to embodiments, as well as additional embodiments of the invention and combinations of various elements and/or steps herein, will be apparent to persons skilled in the art upon reference to this description. It is therefore contemplated that the patented claims will cover any such modifications or embodiments that may fall within the scope of the present invention as defined by the accompanying claims.

What is claimed is:

1. A method of adjusting light output intensity of a display system, wherein the method comprises:
   providing a display system to provide information to a user;
   monitoring dilation of a pupil of the user; and
   adjusting light output intensity of the display system as a function of the monitored dilation of the pupil of the user.

2. The method of claim 1, wherein the display system is used to provide information to a user at a user location, and further wherein the method comprises:
   monitoring ambient light intensity at the user location; and
   adjusting light output intensity of the display system as a function of the monitored ambient light intensity and the monitored dilation of the pupil of the user.

3. The method of claim 2, wherein monitoring dilation of the pupil results in a measurement of pupil size, wherein adjusting light output intensity of the display system comprises:
   calculating expected dilation of the pupil of the user as a function of the monitored ambient light intensity; and
   comparing the measurement of pupil size to the expected dilation of the pupil of the user.

4. The method of claim 1, wherein monitoring dilation of the pupil results in a measurement of pupil size, wherein adjusting light output intensity of the display system comprises:
   comparing the measurement of pupil size to a minimum pupil size; and
   automatically reducing the light output intensity of the display system based on the comparison.

5. The method of claim 4, wherein automatically reducing the light output intensity comprises automatically ceasing light output.

6. The method of claim 1, wherein the display system is used to provide information to a user at a user location, wherein the method further comprises monitoring ambient light intensity at the user location, wherein monitoring dilation of the pupil of the user comprises monitoring dilation of the pupil in ambient light and during use of the display system, wherein adjusting light output intensity of the display system as a function of the monitored dilation of the pupil of the user comprises:
   calculating expected dilation of the pupil of the user as a function of the monitored ambient light intensity and the monitored dilation of the pupil of the user in ambient light;
   comparing the measurement of pupil size during use of the display system to the expected dilation of the pupil of the user; and adjusting the light output intensity of the display system based on the comparison.

7. The method of claim 1, wherein the display system comprises a direct ocular projection system operable for projecting an image to the user.

8. The method of claim 1, wherein the display system comprises at least one of a screen being viewed by the user, a projector, a laser, a heads up display, a vehicle dashboard display, night-sight scope, range finder, and sighting scope.

9. A display system to provide information to a user, the display system comprising:
   a light output device to generate a light output;
   an imaging device operable to capture one or more images of an eye of a user that is using the display system;
   a processing apparatus operable to receive image data from the imaging device representative of one or more images of the eye of the user, wherein the processing apparatus is further operable to:
   determine at least one pupil size measurement using the image data representative of the one or more images of the eye of the user; and
   generate a control signal as a function of the at least one pupil size measurement for use in adjusting light output intensity of the light output device, wherein an intensity of the light output of the light output device is adjustable based on at least the control signal representative of pupil size.

10. The system of claim 9, wherein the system further comprises a light sensor operable to detect ambient light intensity, wherein the processing apparatus is operable to receive an ambient light intensity signal from the light sensor, and further wherein the processing apparatus is operable to generate a control signal as a function of the detected ambient light intensity and the at least one pupil size measurement for use in adjusting light output intensity of the light output device.

11. The system of claim 10, wherein the processing apparatus is further operable to:
   calculate expected dilation of the pupil of the user based on the detected ambient light intensity; and
   compare the at least one pupil size measurement to the expected dilation of the pupil of the user for use in generating the control signal.

12. The system of claim 9, wherein the processing apparatus is further operable to:
   compare the at least one pupil size measurement to a minimum pupil size; and
   automatically reduce the light output intensity of the light output device based on the comparison.

13. The system of claim 9, wherein the processing apparatus is further operable to:
   compare the at least one pupil size measurement to a minimum pupil size; and
   automatically cease light output from the display system based on the comparison.

14. The system of claim 9, wherein the system further comprises a light sensor to detect ambient light intensity, wherein the imaging device is operable to capture one or more images of the eye of the user in ambient light and during use of the display system resulting in at least one pupil size measurement representative of the one or more images of the eye of the user in ambient light and at least one pupil size measurement representative of the one or more images of the eye of the user during use of the display system, and wherein the processing apparatus is operable to:
   calculate expected dilation of the pupil of the user as a function of the detected ambient light intensity and the at least one pupil size measurement representative of the one or more images of the eye of the user in ambient light;
   compare the at least one pupil size measurement representative of the one or more images of the eye of the user during use of the display system to the expected dilation of the pupil of the user; and
   adjust the light output intensity of the display system based on the comparison.

15. The system of claim 9, wherein the display system comprises a direct ocular projection system operable for projecting an image to the user.

16. The system of claim 11, wherein the display system comprises at least one of a screen being viewed by the user, a projector, a laser, a heads up display, a vehicle dashboard display, night-sight scope, range finder, and sighting scope.

17. A display system comprising:
   a light output device operable to generate a light output;
   imaging means for capturing one or more images of an eye of a user using the display system at a location;
   light sensor means for detecting ambient light intensity at the location;
   processing means for receiving an ambient light intensity signal from the light sensor means and image data from the imaging means representative of one or more images of the eye of the user, wherein the processing means further comprises means for determining at least one pupil size measurement using the image data representative of the one or more images of the eye of the user and means for generating a control signal as a function of the detected ambient light intensity and the at least one pupil size measurement for use in adjusting light output intensity of the light output device, wherein an intensity of the light output of the light output device is adjustable based on at least the control signal representative of pupil size.

18. The system of claim 17, wherein the processing means further comprises means for calculating expected dilation of the pupil of the user and comparing the at least one pupil size measurement to the expected dilation of the pupil of the user for use in generating the control signal.

19. The system of claim 17, wherein the processing means further comprises means for comparing the at least one pupil size measurement to a minimum pupil size and means for automatically reducing the light output intensity of the light output device if the measurement is less than minimum pupil size.

20. The system of claim 19, wherein the processing means further comprises means for comparing the at least one pupil size measurement to a minimum pupil size and automatically ceasing light output from the light output device if the measurement is less than minimum pupil size.

* * * * *